United States Patent

Marchese et al.

Patent Number: 5,173,205
Date of Patent: Dec. 22, 1992

[54] SOLID POLYMER ELECTROLYTE BASED ON CROSS-LINKED POLYVINYLETHER

[75] Inventors: Luca Marchese, Milan; Arnaldo Roggero, San Donato Milanese; Maria Andrei, Berceto; Paola Prosperi, Rome, all of Italy

[73] Assignee: Eniricerche S.p.A., Milan, Italy

[21] Appl. No.: 810,288

[22] Filed: Dec. 19, 1991

[30] Foreign Application Priority Data

Dec. 21, 1990 [IT] Italy ................. 22482 A/90

[51] Int. Cl.⁵ .......................... H01G 4/18; H01M 6/18
[52] U.S. Cl. .................... 252/62.2; 252/500; 252/518; 429/192
[58] Field of Search ............ 252/62.2, 518, 500; 429/192

[56] References Cited

U.S. PATENT DOCUMENTS

| | | | |
|---|---|---|---|
| 4,200,701 | 4/1980 | Wetton | 252/62.2 |
| 4,471,037 | 9/1984 | Bannister | 424/192 |
| 4,886,716 | 12/1989 | Roggero | 429/192 |
| 5,064,548 | 11/1991 | Roggero | 252/62.2 |

FOREIGN PATENT DOCUMENTS

| | | |
|---|---|---|
| 0013199 | 7/1980 | European Pat. Off. |
| 2253769 | 7/1975 | France |
| 2568574 | 2/1986 | France |

Primary Examiner—Prince Willis, Jr.
Assistant Examiner—Thomas Steinberg
Attorney, Agent, or Firm—Shea & Gould

[57] ABSTRACT

A solid polymer electrolyte in membrane form, consisting of a solid solution of an ionic compound dissolved in a polyether, is obtained by copolymerizing a vinyl ether with an allyl vinyl ether to obtain a copolymer with allyl unsaturations; hydrosilylating the allyl double bond of this copolymer by reaction with an alkoxysilane to obtain a hydrosilylated copolymer; and cross-linking the hydrosilylated copolymer by means of a diprotic cross-linking agent, operating in solution in an organic solvent in the presence of an ionic compound, and evaporating the solvent to obtain a membrane.

11 Claims, 1 Drawing Sheet

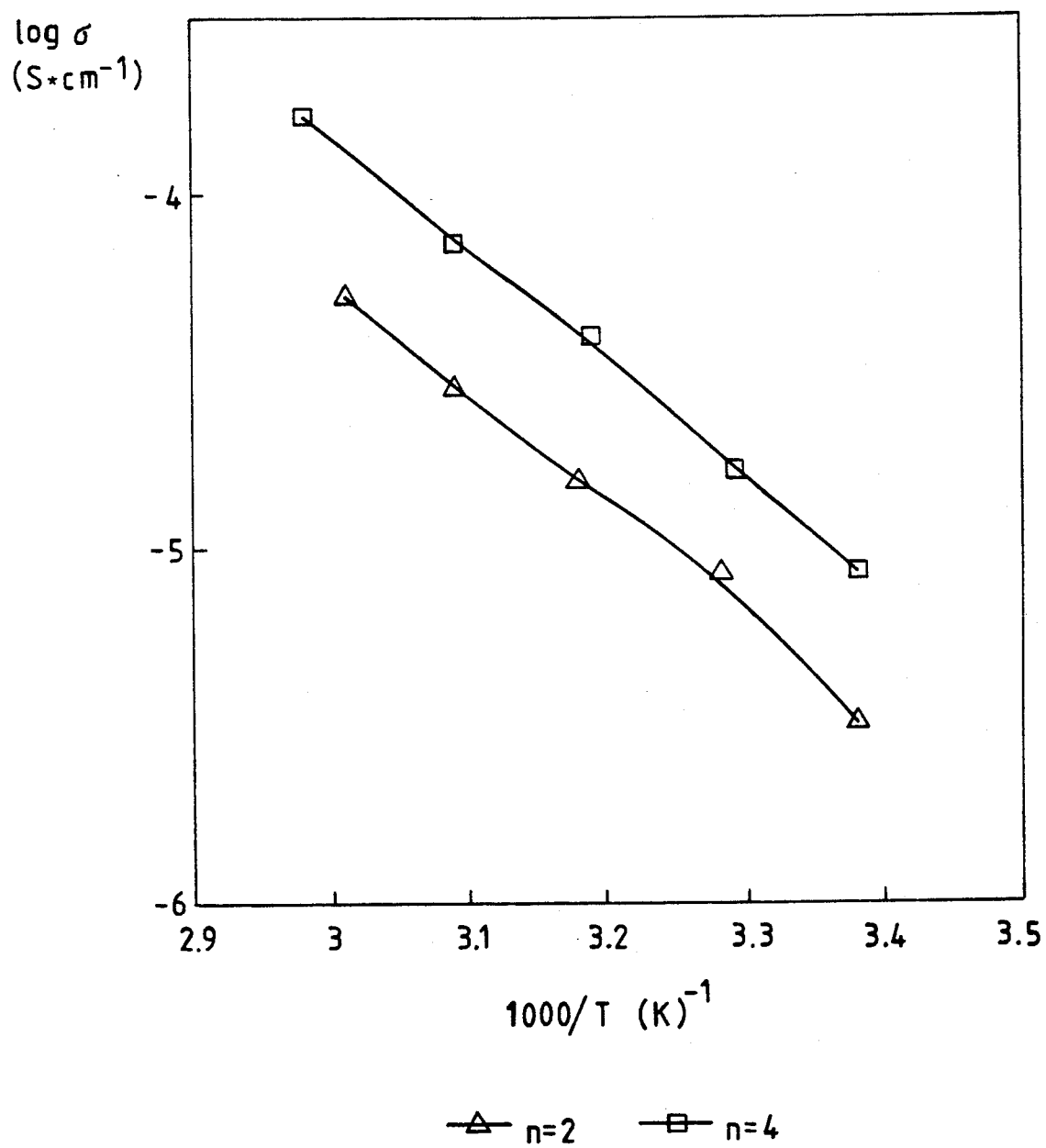

SOLID POLYMER ELECTROLYTE BASED ON CROSS-LINKED POLYVINYLETHER

This invention relates to a solid polymer electrolyte based on cross-linked polyvinylether, the process for its preparation and its use in electrochemical devices which incorporate it.

Solid polymer electrolytes (also known as ion-conducting polymers) are known in the art, and consist of a solid solution of an ionic compound entirely dissolved in a solid plastic macromolecular substance, this latter being the product of polymerizing monomers containing at least one heteroatom, especially oxygen. Said macromolecular material is usually polyethyleneoxide or another polyether, as described for example in U.S. Pat. No. 4,471,037, French patents 2,253,769 and 2,568,574, and European patent 13199.

The problems connected with these solid polymer electrolytes relate generally to the fact that they usually demonstrate an ionic conductivity which is satisfactory only at higher than ambient temperature, and that the electrolytic membranes have poor mechanical strength and poor dimensional stability. All this makes the solid polymer electrolytes of the known art of little interest for practical use.

The object of the present invention is to overcome the aforesaid drawbacks of the known art.

Specifically it has been found, according to the present invention, that a copolymer obtained from a vinyl ether containing ethyleneoxide groups and another vinyl ether which also contains an allyl termination can be hydrosilylated at its allyl unsaturation by reaction with a trialkoxy silane. It has also been found that such a hydrosilylated copolymer is soluble in organic solvents, and can be easily homogenized with ionic compounds and be cross-linked with a diprotic cross-linking agent. An electrolytic membrane can therefore be prepared having excellent mechanical and dimensional characteristics and able to exhibit good ionic conductivity even at relatively low temperature.

In accordance therewith, the present invention firstly provides a solid polymer electrolyte in membrane form, consisting of a solid solution of an ionic compound dissolved in a polyether, characterised in that said electrolyte is obtained by:

a) copolymerizing a vinyl ether of formula:

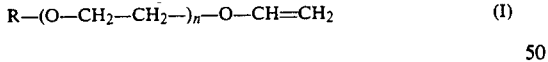

where
R is a methyl or ethyl radical
n is a whole number between 1 and 16,
with an allyl vinyl ether of formula:

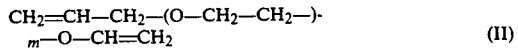

where
m is a whole number between 1 and 10,
the molar ratio of (II) to (I) being between 1/100 and 10/100, to obtain a copolymer having allyl unsaturations;

b) hydrosilylating the allyl double bond of the copolymer obtained in stage a) by reaction with an alkoxysilane chosen from trimethoxy and triethoxy silane, to obtain a hydrosilylated copolymer;

c) cross-linking the hydrosilylated copolymer obtained in stage b) by means of a diprotic cross-linking agent, operating in solution in an organic solvent in the presence of an ionic compound, and evaporating the solvent to obtain a membrane. In stage a) according to the present invention, a copolymer is prepared by cationic polymerization of a vinyl ether (I) and an allyl vinyl ether (II) in the aforestated molar ratios. The vinyl ether (I) can be easily prepared by reacting ethyl vinyl ether with a polyoxyethylene glycol mono-methyl or mono-ethyl ether. The allyl vinyl ether (II) can be easily prepared by reacting an ethylene chlorohydrin vinyl ether (itself prepared by transvinylation of ethylene chlorohydrin) with allyl alcohol operating in a solvent such as dimethylsulphoxide, in the presence of a base such as potassium hydroxide at a temperature of the order of 80° C. The monomers (I) and (II) are obtained with a purity exceeding 99% using normal separation methods. Conveniently, the copolymerization reaction is conducted in an inert solvent at a temperature of about −75°/−80° C. in the presence of a Friedel-Crafts catalyst used in a quantity of between 0.8 and 1.0 moles per 100 moles of the monomers (I) and (II). Examples of catalysts suitable for the purpose are boron trifluoride etherate, aluminium trichloride, alkylaluminium halides and tin tetrachloride. Examples of solvents suitable for the purpose are hydrocarbons such as heptane, benzene and toluene, and chlorinated hydrocarbons such as dichloromethane. Under the aforesaid conditions the polymerization time is of the order of 1-3 hours. On termination of the polymerization the catalyst is deactivated by adding an aliphatic alcohol such as methanol, and the polyvinylether is recovered by normal methods for separating a polymer from an organic solvent solution. The copolymer obtained in this manner can be characterised by analysis techniques such as proton NMR spectra methods, by which the ratio of the comonomers in the copolymer can be determined. The copolymer has a weight-average molecular weight of the order of 20,000-100,000 and a glass transition temperature, determined by DSC, of between −65° and −80° C.

In stage b) of the present invention, the allyl function of the copolymer prepared in stage a) is subjected to hydrosilylation by reacting with an alkoxy silane chosen from trimethoxy and triethoxy silane. In this manner the allyl function in the copolymer is transformed into a function of formula:

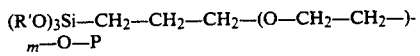

where:
R' indicates methyl or ethyl;
P schematically indicates the polymer.

More specifically, the copolymer after careful drying is functionalized with a trialkoxy silane operating in solution in an anhydrous inert solvent at a temperature of the order of 80°-100° C. in the presence of a catalyst containing a transition metal added in a concentration of the order of ppm (parts per million). Examples of solvents suitable for the purpose are hydrocarbons such as hexane, cyclohexane, benzene and toluene. Examples of catalysts suitable for the purpose are hexachloroplatinic acid, tristriphenyl-phosphine rhodium chloride and dicobalt octacarbonyl. The copolymer functionalization is verified by $^1$H and $^{13}$C NMR spectroscopy, after removing the solvent and the excess trialkoxy silane under vacuum.

In stage c) of the present invention the hydrosilyated copolymer is cross-linked, in the presence of an ionic compound, by suitable diprotic compounds as cross-linking agents, to generate siloxane bridges of type:

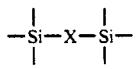

where X can be O or $(O-CH_2-CH_2-)_k-O$, k being a whole number from 1 to 7. The cross-linking agent can be water or an ethylene glycol acidified with HCl and added in a quantity of about 10-20 microliters per gram of polymer. Ionic compounds suitable for this purpose are salts and especially perchlorates, borates, fluoroborates, thiocyanates, trifluoroacetates and trifluoromethanesulphonates of metals (monovalent or polyvalent) and especially lithium, sodium, potassium, calcium, copper, zinc, magnesium, lead, tin and aluminium, used in a quantity such as to achieve an atomic ratio of oxygen in the polyether to metal of between about 4/1 and 18/1. Lithium salts are preferred for the purpose, and in particular lithium perchlorate, in which case the preferred ratio is about 12/1. Stage c) can be conducted by dissolving the hydrosilylated polyvinylether and the ionic compound (preferably a lithium salt) in a suitable anhydrous solvent (preferably acetonitrile) in an inert atmosphere. The cross-linking agent is then added to the solution in a quantity of about 5 times the equivalent reactive sites on the silane in moles. The solution is then poured into a suitable mould, preferably of teflon. The reaction between the alkoxysilane groups and the cross-linking agent takes place during the evaporation of the solvent. This reaction can also be completed after the solvent evaporation, during the drying to eliminate volatile substances, this being achieved by heating to about 40° C. under vacuum. In all cases an insoluble, elastic, transparent membrane of 50-200 micron thickness is obtained having good ionic conductivity at ambient temperature.

The solid polymer electrolyte of the present invention is obtained in this manner, consisting of a solid solution of an ionic compound in the solid polyether cross-linked during membrane formation. This polymer electrolyte can be used as an electrolytic separator in electrochemical devices, as optical and electrochromic displays and as electrochemical generators and sensors.

The following experimental examples are provided to illustrate the invention without in any way representing a limitation to its scope.

EXAMPLE 1

Preparation of the vinyl ether

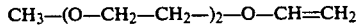

Ethyl vinyl ether (1.8 moles), diethyleneglycol monomethyl ether (0.6 moles) and mercuric acetate ($5.7 \times 10^{-3}$ moles) are fed into a three-neck flask of 500 ml capacity provided with a reflux condenser and maintained under a nitrogen stream. The mixture is heated to reflux temperature and maintained under reflux conditions for 10 hours. During this time the temperature rises from an initial value of 39° C. to a final value of 42° C. The reaction is then extinguished by adding solid potassium carbonate and the mixture distilled firstly at atmospheric pressure to eliminate the excess ethyl vinyl ether and the ethyl alcohol, a by-product of the reaction, and then under reduced pressure (20 torr) to separate the vinyl ether of the title from the unaltered diethyleneglycol monomethyl ether.

The vinyl ether produced in this manner has a purity exceeding 99%, and a yield of about 80% on the initial diethyleneglycol monomethyl ether. The structure is confirmed by NMR and IR spectroscopy and mass spectrometr.

EXAMPLE 2

Preparation of the Diethylene Chlorohydrin Vinyl Ether

315 ml (3.3 moles) of ethyl vinyl ether and 12.5 mmoles of mercuric acetate, which rapidly dissolves, are fed into a three-neck flask of 500 ml capacity provided with a reflux condenser and mechanical stirrer and maintained under a nitrogen stream. 0.660 moles of diethylene chlorohydrin are dripped into the solution, the mixture then being heated under reflux until the ratio (gas-chromatographic analysis) of the chlorohydrin to the corresponding vinyl ether remains constant (20 hours). The mixture is then treated with anhydrous potassium carbonate (20 grams), most of the excess ethyl vinyl ether and by-product ethyl alcohol are removed under vacuum and the remaining mixture is filtered through a Gooch crucible. The filtrate is diluted with chloroform and extracted with water, the organic phase being dried with anhydrous sodium sulphate and filtered. After evaporating the solvent, the crude product is purified by preparative HPLC (stationary phase silica gel).

The chlorohydrin vinyl ether is obtained with a yield of 60% (colourless liquid, purity 99%) and is characterised by mass, FT-IR and NMR spectrometry.

EXAMPLE 3

Preparation of the Allyl Vinyl Ether

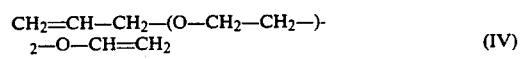

250 ml of dimethylsulphoxide, 55 grams (986 mmoles) of ground potash and 34 ml (500 mmoles) of distilled allyl alcohol are fed into a three-neck flask of 500 ml capacity provided with a reflux condenser and mechanical stirrer and maintained under a nitrogen stream. The mixture is left stirring for 1 hour, after which 62.5 grams (415 mmoles) of ethylene chlorohydrin vinyl ether (III) are dripped in slowly. When the addition is complete the reaction mixture is heated to 80° C. for 2 hours, after which gas chromatographic analysis shows that the reaction is complete. The mixture is treated by pouring the flask contents into cold water (about 500 ml) and extracting with three 250 ml portions of chloroform. The pooled organic phases are washed with water until neutral and then dried with anhydrous sodium sulphate. The chloroform is removed in a rotary evaporator, after which the crude reaction product, about 40 grams of yellowish oil, is distilled under vacuum (0.01 mmHg), to finally obtain 30 grams of pure diethyleneglycol allyl vinyl ether (colourless liquid). The structure is confirmed by mass, FT-IR, $^1H$ and $^{13}C$ NMR spectrometry.

EXAMPLE 4

Copolymerization of Vinyl Ether and Allyl Vinyl Ether 58 mmoles of monovinyl ether of Example 1 and 1.16 mmoles of allyl vinyl ether of Example 3 dissolved in 20 ml of anhydrous methylene chloride are fed into a reactor in the form of a 50 ml test tube fitted with a spiral mechanical stirrer and nitrogen and reagent feed inlets. The mixture is cooled to −78° C. and 0.63 mmoles of BF$_3$ etherate dissolved in 2 ml of anhydrous CH$_2$Cl$_2$ are added under vigorous stirring. A certain increase in viscosity is observed after 45 minutes. After 2 hours the viscosity is high and turbidity is observed. The polymerization is then interrupted by adding an excess of methanol (2 ml) and the product allowed to reach ambient temperature, on which it is taken up in methylene chloride and poured into 100 ml of water and bicarbonate, the organic phase being separated, washed with water and finally dried with sodium sulphate. After solvent removal and prolonged treatment at 50° C. under vacuum (0.01 mmHg) a colourless sticky product is obtained. The yield is quantitative. The copolymer is characterized by FT-IR and NMR spectroscopy, confirming the presence of the allyl function bonded to the polymer. DSC analysis confirms that the polymer is amorphous (Tg=−71° C.).

EXAMPLE 5

Hydrosilylation of the Copolymer

The copolymer solution (5 grams in 20 ml of anhydrous toluene) obtained by the procedure described in Example 4 is fed into a 50 ml tailed test tube in a nitrogen atmosphere, after which an excess of triethoxy silane (2.5 mmoles) over the molar double bond content (4:1) is added, finally injecting 50 microliters of a 3.3% hexachloroplatinic acid (H$_2$PtCl$_6$) solution in isopropanol. The reactor is hermetically sealed with a screw stopper and the nitrogen flow interrupted. The reaction is conducted for 7 hours at 100° C., the mixture left to return to ambient temperature and then siphoned under nitrogen into a 250 ml flask. The solvent and the excess triethoxy silane are removed under vacuum (0.01 mmHg) by heating to 45° C. for several hours. The polymer maintains the same appearance as the starting material and is only slightly coloured. Characterisation by FT-IR and NMR confirms the disappearance of the double bonds, the presence of the bonded triethoxysilane group and the absence of Si-H groups.

EXAMPLE 6

Preparation of the Electrolytic Membrane

The hydrosilylated polyvinylether-based electrolytic membrane is prepared by the following procedure conducted in a glove box in an argon atmosphere:

a solution consisting of the hydrosilylated polyvinylether and the lithium salt in acetonitrile is prepared;

a small quantity of water or ethyleneglycol acidified with HCl is added to this solution and the mixture is homogenized at ambient temperature;

the solution obtained is poured into teflon moulds and the moulds placed in an argon forced circulation chamber to gradually remove the solvent and other volatile substances;

after some days, necessary for completion of the cross-linking reaction, the electrolytic membrane is heated to 40° C. under reduced pressure for 4 or 5 hours.

In this manner a transparent homogeneous membrane of about 100 micron thickness is obtained which can be easily removed from the teflon mould and made to adhere to the surface of the electrode used for the conductivity measurements.

Confirmation of the cross-linking of the polymer subjected to this treatment is confirmed by the evident improvement in the mechanical characteristics of the material and the fact that when such membranes are re-treated with acetonitrile they swell. This method was used specifically to prepare an electrolytic membrane from 1 grams of the copolymer of Example 5 and a quantity of LiClO$_4$ such as to obtain an EO(ethyleneoxide)/Li ratio of 10. The two components are dissolved in 10 ml of anhydrous acetonitrile in an argon atmosphere; 20 microliters of diethyleneglycol acidified with HCl (0.05 mmoles per mmole of diethyleneglycol) are added to the solution as cross-linking agent. In an identical manner an electrolytic membrane is prepared from a polymer containing a vinyl ether (I) where n=4. These membranes are about 100 micron thick. The conductivity of the membranes at various temperatures is shown on the graph of the FIGURE (n=2 for 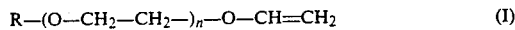 and n=4 for 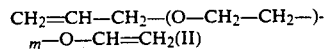).

The electrolytic membranes are amorphous and have glass transition temperatures of about −40° C.

We claim:

1. A solid polymer electrolyte in membrane form, consisting of a solid solution of an ionic compound dissolved in a polyether, characterised in that said electrolyte is obtained by:

a) copolymerizing a vinyl ether of formula:

$$R-(O-CH_2-CH_2-)_n-O-CH=CH_2 \qquad (I)$$

where

R is a methyl or ethyl radical n is a whole number between 1 and 16, with an allyl vinyl ether of formula:

$$CH_2=CH-CH_2-(O-CH_2-CH_2-)_m-O-CH=CH_2 \qquad (II)$$

where m is a whole number between 1 and 10, the molar ratio of (II) to (I) being between 1/100 and 10/100, to obtain a copolymer having allyl unsaturations;

b) hydrosilylating the allyl double bond of the copolymer obtained in stage a) by reaction with an alkoxysilane chosen from trimethoxy and triethoxy silane, to obtain a hydrosilylated copolymer;

c) cross-linking the hydrosilylated copolymer obtained in stage b) by means of a diprotic cross-linking agent, operating in solution in an organic solvent containing an ionic compound, and evaporating the solvent to obtain a membrane.

2. A solid polymer electrolyte as claimed in claim 1, characterised in that in stage a) the copolymer is prepared by cationic polymerization in an inert solvent at a temperature of about −75°/−80° C. in the presence of a Friedel-Crafts catalyst in a quantity of between 0.8 and 1.0 moles per 100 moles of the monomers (I) and (II), the copolymer obtained having a weight-average molecular weight of the order of 20,000–100,000 and a glass transition temperature of between −65° and −80° C.

3. A solid polymer electrolyte as claimed in claim 1, characterised in that in stage b) the copolymer prepared in stage a) is reacted with an alkoxy silane chosen from trimethoxy and triethoxy silane, operating in solution in an anhydrous inert solvent at a temperature of the order of 80°–100° C. in the presence of a catalyst containing a transition metal.

4. A solid polymer electrolyte as claimed in claim 1, characterised in that in stage c) the hydrosilylated copolymer is cross-linked, using a cross-linking agent chosen from water and an ethyleneglycol acidified with HCl and added in a quantity of about 10–20 microliters per gram of copolymer, operating in an organic solvent and containing a metal salt and, in a quantity such as to achieve an atomic ratio of oxygen in the polyether to metal of between about 4/1 and 18/1.

5. A solid polymer electrolyte as claimed in claim 4, characterised in that the metal salt is a lithium salt, the atomic ratio of oxygen in the polyether to lithium being of the order of 12/1.

6. A solid polymer electrolyte as claimed in claim 4, characterised in that the solution is poured into a mould, the solvent is evaporated and the evaporation residue dried to obtain a membrane having a thickness of between 50 and 200 micron.

7. An electrochemical device containing the solid polymer electrolyte claimed in claim 1.

8. A solid polymer electrolyte as claimed in claim 4, wherein in step C the organic solvent is acetonitrile.

9. A solid polymer electrolyte as claimed in claim 1, wherein in Step C, the metal salt is selected from the group consisting of perchlorates, borates, fluoroborates, thiocyanates, trifluoroacetates and trifluoromethanesulphonates.

10. A solid polymer electrolyte as claimed in claim 9, wherein the metal is selected from the group consisting of lithium, sodium, potassium, calcium, copper, zinc, magnesium, lead, tin and aluminum.

11. A solid polymer electrolyte as claimed in claim 5, wherein the lithium salt is lithium perchlorate.

* * * * *